US011857803B2

(12) United States Patent
Arazi et al.

(10) Patent No.: US 11,857,803 B2
(45) Date of Patent: Jan. 2, 2024

(54) DIFFUSING ALPHA-EMITTER RADIATION THERAPY WITH ENHANCED BETA TREATMENT (71) Applicant: ALPHA TAU MEDICAL LTD., Jerusalem (IL)

(72) Inventors: Lior Arazi, Tel Aviv (IL); Robert B Den, Merion Station, PA (US); Michael Schmidt, Kfar Saba (IL); Ofer Magen, Hod Hasharon (IL); Itzhak Kelson, Tel Aviv (IL); Amnon Gat, Matan (IL)

(73) Assignee: ALPHA TAU MEDICAL LTD., Jerusalem (IL)

(*) Notice: Subject to any disclaimer, the term of this patent is extended or adjusted under 35 U.S.C. 154(b) by 59 days.

(21) Appl. No.: 17/549,929

(22) Filed: Dec. 14, 2021

(65) Prior Publication Data
US 2022/0184418 A1 Jun. 16, 2022

Related U.S. Application Data (60) Provisional application No. 63/126,070, filed on Dec. 16, 2020.

(51) Int. Cl.
*A61N 5/10* (2006.01)
(52) U.S. Cl.
CPC .... *A61N 5/1027* (2013.01); *A61N 2005/1085* (2013.01); *A61N 2005/1098* (2013.01)
(58) Field of Classification Search
None
See application file for complete search history.

(56) References Cited

U.S. PATENT DOCUMENTS

| 3,754,999 A | 8/1973 | Merges |
| 3,811,426 A | 5/1974 | Culver et al. |
| 4,107,283 A | 8/1978 | Pratt et al. |
| 4,652,459 A | 3/1987 | Engelhardt |
| 4,697,575 A | 10/1987 | Horowitz |
| 4,976,680 A | 12/1990 | Hayman et al. |
| 5,205,289 A | 4/1993 | Hardy et al. |
| 5,342,283 A | 8/1994 | Good |
| 5,531,662 A | 7/1996 | Carr |
| 5,713,828 A | 2/1998 | Coniglione |
| 5,716,317 A | 2/1998 | Okano et al. |

(Continued)

FOREIGN PATENT DOCUMENTS

| CN | 101259290 A | 9/2008 |
| CN | 101437467 A | 5/2009 |

(Continued)

OTHER PUBLICATIONS

Arazi et al., "The Treatment of Solid Tumors by Alpha Emitters Released from (224)Ra-loaded Sources—Internal Dosimetry Analysis," Physics in Medicine and Biology, vol. 55, pp. 1203-1218, year 2010.

(Continued)

*Primary Examiner* — Thaddeus B Cox
(74) *Attorney, Agent, or Firm* — Kligler & Associates Patent Attorneys Ltd.

(57) ABSTRACT

An interstitial source including a base suitable for implanting in a tumor and alpha emitting atoms attached to the base, with a concentration of at least 6 μCi per centimeter length. The alpha emitting atoms are attached to the base, with a desorption probability upon radioactive decay of not more than 30%.

32 Claims, 1 Drawing Sheet

(56) References Cited

U.S. PATENT DOCUMENTS

| | | |
|---|---|---|
| 6,030,333 A | 2/2000 | Sioshansi et al. |
| 6,059,714 A | 5/2000 | Armini et al. |
| 6,060,036 A | 5/2000 | Armini |
| 6,077,413 A | 6/2000 | Haefeli et al. |
| 6,099,458 A | 8/2000 | Robertson |
| 6,224,536 B1 | 5/2001 | Pike |
| 6,248,057 B1 | 6/2001 | Mavity et al. |
| 6,254,552 B1 | 7/2001 | Lewis et al. |
| 6,391,911 B1 | 5/2002 | Bases |
| 6,392,068 B1 | 5/2002 | Lu et al. |
| 6,394,945 B1 | 5/2002 | Chan et al. |
| 6,475,644 B1 | 11/2002 | Hampikian et al. |
| 6,575,888 B2 | 6/2003 | Zamora et al. |
| 6,589,502 B1 | 7/2003 | Coniglione et al. |
| 6,635,234 B1 | 10/2003 | Larsen et al. |
| 6,638,205 B1 | 10/2003 | Chan et al. |
| 6,666,811 B1 | 12/2003 | Good |
| 6,676,595 B1 | 1/2004 | Delfino |
| 6,709,693 B1 | 3/2004 | Dinkelborg et al. |
| 6,716,156 B2 | 4/2004 | Menuhr et al. |
| 6,723,052 B2 | 4/2004 | Mills |
| 8,821,364 B2 | 9/2014 | Fisher et al. |
| 8,834,837 B2 | 9/2014 | Kelson et al. |
| 8,894,969 B2 | 11/2014 | Kelson et al. |
| 10,166,403 B2 | 1/2019 | Bakker et al. |
| 2001/0005930 A1 | 7/2001 | Coniglione |
| 2001/0006616 A1 | 7/2001 | Leavitt |
| 2002/0055666 A1 | 5/2002 | Hunter et al. |
| 2002/0055667 A1 | 5/2002 | Mavity et al. |
| 2002/0077520 A1 | 6/2002 | Segal et al. |
| 2002/0131935 A1 | 9/2002 | Fisher et al. |
| 2003/0092957 A1 | 5/2003 | Scott et al. |
| 2003/0118649 A1 | 6/2003 | Gao et al. |
| 2004/0018968 A1 | 1/2004 | Sgouros et al. |
| 2004/0076579 A1 | 4/2004 | Coniglione et al. |
| 2004/0208821 A1 | 10/2004 | Larsen et al. |
| 2004/0242953 A1 | 12/2004 | Good |
| 2005/0080314 A1 | 4/2005 | Terwilliger et al. |
| 2005/0159809 A1 | 7/2005 | Hezi-Yamit et al. |
| 2005/0222013 A1 | 10/2005 | Jung et al. |
| 2006/0014938 A1 | 1/2006 | Groman et al. |
| 2006/0039858 A1 | 2/2006 | Dadachova et al. |
| 2006/0142853 A1 | 6/2006 | Wang et al. |
| 2006/0224035 A1 | 10/2006 | Russell, Jr. et al. |
| 2006/0269475 A1 | 11/2006 | Ryu et al. |
| 2007/0041900 A1 | 2/2007 | Kelson et al. |
| 2008/0193374 A1 | 8/2008 | Larsen et al. |
| 2008/0249398 A1 | 10/2008 | Harder et al. |
| 2009/0136422 A1 | 5/2009 | Kelson et al. |
| 2009/0234175 A1 | 9/2009 | Maier |
| 2009/0311173 A1 | 12/2009 | Kelson et al. |
| 2009/0311413 A1 | 12/2009 | Kelson et al. |
| 2010/0015042 A1 | 1/2010 | Keisari et al. |
| 2010/0056844 A1 | 3/2010 | Fisher et al. |
| 2010/0062143 A1 | 3/2010 | Kelson et al. |
| 2010/0178245 A1 | 7/2010 | Arnsdorf et al. |
| 2010/0200778 A1 | 8/2010 | Drobnik et al. |
| 2011/0184283 A1 | 7/2011 | Rivard |
| 2012/0123189 A1 | 5/2012 | Ribbing et al. |
| 2013/0225901 A1 | 8/2013 | Krishnan et al. |
| 2013/0253255 A1 | 9/2013 | Van Niekerk |
| 2014/0296612 A1 | 10/2014 | Schwartz |
| 2015/0104560 A1 | 4/2015 | Kelson et al. |
| 2015/0292061 A1 | 10/2015 | Fassbender et al. |
| 2016/0250360 A1 | 1/2016 | Larsen |
| 2017/0058360 A1 | 3/2017 | Theodorescu et al. |
| 2017/0319871 A1 | 11/2017 | Pitman |
| 2018/0345038 A1 | 12/2018 | Kelson et al. |
| 2019/0022410 A1 | 1/2019 | Hermann et al. |
| 2019/0099620 A1 | 4/2019 | Isola et al. |
| 2020/0114004 A1 | 4/2020 | Tuli |
| 2021/0008233 A1 | 1/2021 | Kelson et al. |

FOREIGN PATENT DOCUMENTS

| | | |
|---|---|---|
| EP | 1191121 A1 | 3/2002 |
| EP | 1232769 A1 | 8/2002 |
| EP | 1815873 A1 | 8/2007 |
| RU | 2089143 C1 | 9/1997 |
| RU | 2182022 C1 | 5/2002 |
| RU | 2606108 C2 | 1/2017 |
| WO | 9719706 A1 | 6/1997 |
| WO | 9719724 A1 | 6/1997 |
| WO | 9733628 A1 | 9/1997 |
| WO | 9902194 A1 | 1/1999 |
| WO | 9917812 A1 | 4/1999 |
| WO | 9921615 A1 | 5/1999 |
| WO | 0006243 A2 | 2/2000 |
| WO | 0040275 A2 | 7/2000 |
| WO | 0071204 A1 | 11/2000 |
| WO | 0160417 A2 | 8/2001 |
| WO | 0205859 A2 | 1/2002 |
| WO | 00241923 A1 | 5/2002 |
| WO | 02068000 A2 | 9/2002 |
| WO | 2004026111 A2 | 4/2004 |
| WO | 2004045549 A2 | 6/2004 |
| WO | 2004096293 A2 | 11/2004 |
| WO | 2006003123 A2 | 1/2006 |
| WO | 2006043083 A2 | 4/2006 |
| WO | 2006110889 A2 | 10/2006 |
| WO | 2007013060 A1 | 2/2007 |
| WO | 2007013060 A2 | 2/2007 |
| WO | 2011018792 A1 | 2/2011 |
| WO | 2015142316 A1 | 9/2015 |
| WO | 2016205652 A1 | 12/2016 |
| WO | 2018207105 A1 | 11/2018 |
| WO | 2019171308 A1 | 9/2019 |
| WO | 2019193464 A1 | 10/2019 |
| WO | 2020089819 A1 | 5/2020 |
| WO | 2022148985 A1 | 7/2022 |

OTHER PUBLICATIONS

Arazi, "Diffusing Alpha-Emitters Radiation Therapy: Theoretical and Experimental Dosimetry," PH.D. Thesis, Raymond and Beverly Sackler Faculty of Exact Sciences, School of Physics and Astronomy, Tel Aviv University, pp. 1-285, Sep. 2008.
Kelson et al., U.S. Appl. No. 17/343,784, filed Jun. 10, 2021.
Kelson et al., U.S. Appl. No. 17/141,251, filed Jan. 5, 2021.
Kelson et al., U.S. Appl. No. 17/343,786, filed Jun. 10, 2021.
Kelson et al., U.S. Appl. No. 17/343,773, filed Jun. 10, 2021.
Kelson et al., U.S. Appl. No. 17/343,779, filed Jun. 10, 2021.
Kelson et al., U.S. Appl. No. 17/343,783, filed Jun. 10, 2021.
Kelson et al., U.S. Appl. No. 17/343,781, filed Jun. 10, 2021.
Kelson et al., U.S. Appl. No. 17/343,789, filed Jun. 10, 2021.
GE Healthcare, "Typhoon FLA 9000 Biomolecular Imager," Data File 28-9610-72 AB, General Electric Company, pp. 1-8, years 2009-2010.
The University of Arizona: "Startup with an Innovative Imaging System Wins Sponsored Launch," News, Tech Parks Arizona, pp. 1-4, year 2020.
"Imaging Plates", Product Description, pp. 1-15, Jun. 12, 2007 Downloaded from https://www.buero-analytik-winden.de/app/download/13602912/Imaging+plates+ausf%C3%BChrliche+Beschreibung.pdf.
Kelson et al., U.S. Appl. No. 18/094,424, filed Jan. 9, 2023.
Kelson et al., U.S. Appl. No. 18/094,421, filed Jan. 9, 2023.
Kelson et al., U.S. Appl. No. 18/094,419, filed Jan. 9, 2023.
Kelson et al., U.S. Appl. No. 18/094,416, filed Jan. 9, 2023.
Kelson et al., U.S. Appl. No. 18/094,411, filed Jan. 9, 2023.
Kelson et al., U.S. Appl. No. 18/094,408, filed Jan. 9, 2023.
Kelson et al., U.S. Appl. No. 18/094,429, filed Jan. 9, 2023.
Kelson et al., U.S. Appl. No. 18/094,406, filed Jan. 9, 2023.
U.S. Appl. No. 18/094,416 Office Action dated Apr. 12, 2023.
U.S. Appl. No. 18/094,406 Office Action dated Apr. 24, 2023.
U.S. Appl. No. 18/094,421 Office Action dated May 9, 2023.
U.S. Appl. No. 18/094,411 Office Action dated May 9, 2023.
AU Application # 2022204082 Office Action dated May 22, 2023.

(56) References Cited

OTHER PUBLICATIONS

AU Application # 2022204083 Office Action dated May 22, 2023.
AU Application # 2022204084 Office Action dated May 22, 2023.
U.S. Appl. No. 18/094,429 Office Action dated Jun. 14, 2023.
U.S. Appl. No. 18/094,419 Office Action dated Jun. 16, 2023.
U.S. Appl. No. 18/094,424 Office Action dated Jun. 16, 2023.
U.S. Appl. No. 18/094,408 Office Action dated Jun. 16, 2023.
CN Application # 2019800233036 Office Action dated Jan. 12, 2022.
U.S. Appl. No. 16/610,507 Office Action dated Mar. 29, 2022.
Perry et al., "A method for testing the diffusion coefficient of polymer films", 1996 AARST International Radon Symposium, pp. 1-9, Sep. 29-Oct. 2, 1996.
JP Application # 2020-551517 Office Action dated Nov. 30, 2022.
CN Application # 2018800298271 Office Action dated Mar. 30, 2022.
International Application # PCT/IB2021/061687 Search Report dated Apr. 10, 2022.
JP Application # 2019557389 Office Action dated May 24, 2022.
RU Application # 2020130217 Office Action dated Jun. 3, 2022.
Popovtzer et al., "Initial Safety and Tumor Control Results from a "First-in-Human" Multicenter Prospective Trial Evaluating a Novel Alpha-Emittig Radionuclide for the Tretament of Locally Advanced Recurrent Squamous Cell Carcinomas of the Skin and Head and Neck," International Journal of Radiation Oncology—Biology—Physics, vol. 106, issue 3, pp. 571-578, Mar. 1, 2020.
Arazi, "Diffusing Alpha-Emitters Radiation Therapy: Approximate Modeling of the Macroscopic Alpha Particle Dose of a Point Source," Physics in Medicine & Biology, vol. 65, issue 1, pp. 1-24, year 2020.
Feliciani et al., "Diffusing Alpha-Emitters Radiation Therapy (DaRT): Template Based Treatment Planning Technique for Brachytherapy of Squamous Cell Skin Cancer," Abstracts/Physica Medica, vol. 52, p. 35, year 2018.
Arazi et al., "Diffusing Alpha Emitters Radiation Therapy: Theoretical Modeling," International Journal of Radiation Oncology—Biology—Physics, Pergamon Press, vol. 108, No. 3, p. e336, Oct. 23, 2020.
Arazi et al., "Alpha DaRT: Revoluionary Alpha-Emitters Brachytherapy," Journal of Medical Imaging and Radiation Sciences, Elsevier, Amsterdam, NL, vol. 50, No. 4, p. S96, Dec. 1, 2019.
European Application # 22178053.9 Search report dated Nov. 3, 2022.
U.S. Appl. No. 17/343,786 Office Action dated Oct. 6, 2022.
International Application # PCT/IB2022/055322 Search Report dated Nov. 15, 2022.
EP Application # 22178051.3 Search Report dated Nov. 2, 2022.
U.S. Appl. No. 17/343,781 Office Action dated Sep. 21, 2022.
International Application # PCT/IB2022/055325 Search Report dated Nov. 17, 2022.
U.S. Appl. No. 17/343,779 Office Action dated Sep. 16, 2022.
International Application # PCT/IB2022/055324 Search Report dated Nov. 17, 2022.
EP Application # 22178060.4 Search Report dated Nov. 3, 2022.
U.S. Appl. No. 17/343,773 Office Action dated Sep. 19, 2022.
International Application # PCT/IB2022/055323 Search Report dated Nov. 15, 2022.
U.S. Appl. No. 17/343,783 Office Action dated Sep. 16, 2022.
International Application # PCT/IB2022/055326 Search Report dated Nov. 17, 2022.
U.S. Appl. No. 17/343,784 Office Action dated Sep. 21, 2022.
International Application # PCT/IB2022/055327 Search Report dated Nov. 20, 2022.
U.S. Appl. No. 17/343,789 Office Action dated Sep. 16, 2022.
International Application # PCT/IB2022/055328 Search Report dated Nov. 20, 2022.
International Application # PCT/IB2022/055329 Search Report dated Nov. 21, 2022.
SG Application # 11201910176P Office Action dated Aug. 1, 2022.
ARIPO Application # AP/P/2019011968 Office Action dated Sep. 8, 2022.
ARIPO Application # AP/P/2020012678 Office Action dated Sep. 12, 2022.
CN Application # 2019800233036 Office Action dated Sep. 20, 2022.
U.S. Appl. No. 16/979,543 Office Action dated Oct. 12, 2022.
De Kruijff et al., "A Critical Review of Alpha Radionuclide Theraphy—How to Deal with Recoiling Daughters?", Pharmaceuticals, vol. 8, No. 2, pp. 321-336, year 2015.
Meyer et al., "Inhibition of neointimal proliferation with 188Re-labeled self-expanding nitinol stent in a sheep model", Radiology, vol. 229, issue 3, pp. 847-854, Dec. 2003.
Cooks et al., "Local Control of Lung Derived Tumors by Diffusing Alpha-Emitting Atoms Released From Intratumoral Wires Loaded With Radium-224", International Journal of Radiation Oncology*Biology*Physics, vol. 74, Issue 3, pp. 966-973, Jul. 1, 2009.
Arazi et al., "Treatment of solid tumors by interstitial release of recoiling short-lived alpha emitters", Physics in Medicine Biology, vol. 52, issue 16, pp. 5025-5042, Aug. 1, 2007.
Cooks et al., "Growth retardation and destruction of experimental squamous cells carcinoma by interstitial radioactive wires releasing diffusing alpha-emitting atoms", International Journal of Cancer, vol. 122, issue 7, pp. 1657-1664, Apr. 1, 2008.
Cooks et al., "Interstitial wires releasing diffusing alpha emitters combined with chemotherapy improved local tumor control and survival in squamous cell carcinoma-bearing mice", Cancer, vol. 115, issue 8, pp. 1791-1801, Apr. 15, 2009.
Thomson et al., "Stereotactic Multiple are Radiotherapy", British Journal of Radiology, vol. 63, issue 754, pp. 745-751, year 1990.
Orre et al., "Hyperfine interaction studies of radon in some metals and metal oxides with the alpha-gamma angular correlation method", Uppsala University, Institute of Physics, pp. 1-89, Nov. 1975.
Wood., "Displacement current and multiple pulse effects in plasma source ion implantation", Journal of Applied Physics, vol. 73, issue 10, pp. 4770-4778, May 15, 1993.
Free Dictionary "Embed", The Free Dictionary, p. 1-1, year 2012.
Kirby et al., "The Radiochemistry of Radium", National Academy of Sciences, National Research Council, Nuclear Science Series, U.S Atomic Energy Commission, pp. 1-213, Dec. 1964.
Milkey, R., "Stability of Dilute Solutions of Uranium, Lead, and Thorium Ions", Analytical Biochemistry, vol. 26, pp. 1800-1803, year 1954.
Stajnkrycer et al., "Chemical and Radiological Toxicity of Depleted Uranium", Military Medicine, vol. 169, issue 3, pp. 212-216, Mar. 2004.
Tepe et al., "Prophylaxis of Restenosis With 186Re-Labeled Stents in a Rabbit Model", Circulation, vol. 104, pp. 480-485, year 2001.
Abildskov et al., "Hyperfine interactions of 220RN and 224RA implanted into Fe, Al, Cd and Bi metals", Nuclear Physics, issue A194, pp. 292-304, year 1972.
Dillman et al., "A Randomized Trial of Induction Chemotherapy plus High-Dose Radiation versus Radiation Alone in Stage III Non-Small-Cell Lung Cancer", The New England Journal of Medicine, vol. 323, issue 14, pp. 940-945, Oct. 4, 1990.
Le Chevalier et al., "Radiotherapy alone versus combined chemotherapy and radiotherapy in nonresectable non-small-cell lung cancer: first analysis of a randomized trial in 353 patients", Journal of National Cancer Institute, vol. 83, No. 6, pp. 417-423, Mar. 20, 1991.
Al-Sarraf et al., "Concurrent radiotherapy and chemotherapy with cisplatin in inoperable squamous cell carcinoma of the head and neck", An RTOG Study, Cancer, vol. 59, issue 2, pp. 259-265, Jan. 15, 1987.
O'Connell et al., "Improving adjuvant therapy for rectal cancer by combining protracted-infusion fluorouracil with radiation therapy after curative surgery", The New England Journal of Medicine, vol. 331, issue 8, pp. 502-507, Aug. 25, 1994.
Wolff et al., "Phase I trial of gemcitabine combined with radiation for the treatment of locally advanced pancreatic adenocarcinoma", Clinical Cancer Research, vol. 7, issue 8, pp. 2246-2253, Aug. 7, 2001.

(56) References Cited

OTHER PUBLICATIONS

Popovtzer et al., "Alpha-Particle Based Brachytherapy Treatment of Patients with Squamous Cell Carcinoma, a New Effective Concept", vol. 17, Issue 4, Supplement, p. S43, Aug. 31, 2018.
Wikipedia, "Radium", pp. 1-11, Mar. 5, 2017.
JP Application # 2020551517 Office Action dated Aug. 16, 2023.
CN Application # 2019800233036 Office Action dated Oct. 10, 2023.
U.S. Appl. No. 18/094,406 Office Action dated Aug. 21, 2023.
U.S. Appl. No. 18/094,408 Office Action dated Oct. 10, 2023.
U.S. Appl. No. 18/094,411 Office Action dated Aug. 21, 2023.
U.S. Appl. No. 18/094,416 Office Action dated Sep. 29, 2023.
U.S. Appl. No. 18/094,419 Office Action dated Oct. 10, 2023.
U.S. Appl. No. 18/094,421 Office Action dated Aug. 22, 2023.
U.S. Appl. No. 18/094,424 Office Action dated Oct. 10, 2023.
U.S. Appl. No. 18/094,429 Office Action dated Sep. 29, 2023.

DIFFUSING ALPHA-EMITTER RADIATION THERAPY WITH ENHANCED BETA TREATMENT

CROSS-REFERENCE TO RELATED APPLICATIONS

The present application claims the benefit of U.S. Provisional Application 63/126,070, entitled "Diffusing Alpha-emitters Radiation Therapy with Enhanced Beta Treatment", filed on Dec. 16, 2020, whose disclosure is incorporated herein by reference in its entirety.

FIELD OF THE INVENTION

The present invention relates generally to radiotherapy and particularly to apparatus and methods for providing implantable radiation sources with combined alpha and non-alpha radiation.

BACKGROUND OF THE INVENTION

Ionizing radiation is commonly used in the treatment of certain types of tumors, including malignant cancerous tumors, to destroy their cells. Ionizing radiation, however, can also damage healthy cells of a patient, and therefore care is taken to minimize the radiation dose delivered to healthy tissue outside of the tumor, while maximizing the dose to the tumor.

Ionizing radiation destroys cells by creating damage to their DNA. The biological effectiveness of different types of radiation in killing cells is determined by the type and severity of the DNA lesions they create. Alpha particles are a powerful means for radiotherapy since they induce clustered double-strand breaks on the DNA, which cells cannot repair. Unlike conventional types of radiation, the destructive effect of alpha particles is also largely unaffected by low cellular oxygen levels, making them equally effective against hypoxic cells, whose presence in tumors is a leading cause of failure in conventional radiotherapy based on photons or electrons. In addition, the short range of alpha particles in tissue (less than 100 micrometers) ensures that if the atoms which emit them are confined to the tumor volume, surrounding healthy tissue will be spared.

Diffusing alpha-emitters radiation therapy (DaRT), described for example in U.S. Pat. No. 8,834,837 to Kelson, extends the therapeutic range of alpha radiation, by using radium-223 or radium-224 atoms, which generate chains of several radioactive decays with a governing half-life of 3.6 days for radium-224 and 11.4 days for radium-223. In DaRT, the radium atoms are attached to a source (also referred to as a "seed") implanted in the tumor with sufficient strength such that they do not leave the source in a manner that they go to waste (by being cleared away from the tumor through the blood), but a substantial percentage of their daughter radionuclides (radon-220 in the case of radium-224 and radon-219 in the case of radium-223) leave the source into the tumor, upon radium decay. These radionuclides, and their own radioactive daughter atoms, spread around the source by diffusion up to a radial distance of a few millimeters before they decay by alpha emission. Thus, the range of destruction in the tumor is increased relative to radionuclides which remain with their daughters on the source.

In addition to releasing alpha radiation, some of the daughter atoms release beta radiation. The beta radiation is much weaker than the alpha radiation, and has a longer range than the alpha radiation.

In order for the treatment of a tumor to be effective, DaRT seeds employed in the treatment should release a sufficient number of radon atoms to destroy the tumor with a high probability. If an insufficient amount of radiation is employed, too many cancerous cells will remain in the tumor, and these cells may reproduce to reform the malignant tumor. On the other hand, the seeds should not release too many radon atoms, as some of their daughters are cleared from the tumor through the blood and could therefore damage distant healthy tissue, including organs such as bone marrow, kidneys and/or ovaries of a patient.

The amount of radium atoms on the DaRT source is quantified in terms of the activity, i.e., the rate of radium decays. The DaRT source activity is measured in units of micro-Curie ($\mu$Ci) or kilo-Becquerel (kBq), where 1 $\mu$Ci=37 kBq=37,000 decays per second. When using DaRT, the radiation dose delivered to the tumor cells depends not only on the radium activity of the source, but also on the probability that the radium or its daughter radon atoms will leave the source into the tumor. The probability that the daughter radon atoms will leave the source into the tumor upon radium's alpha decay is referred to herein as the "desorption probability". If the rate of diffusion of radium from the source is negligible, instead of referring to the activity of the source, one can use the "radon release rate", which is defined herein as the product of activity on the source and the desorption probability of radon from the source, as a measure of the DaRT related activity of a source. Like the activity, the radon release rate is given in $\mu$Ci or kBq. The activity and radon release rate values given herein are, unless stated otherwise, of the source at the time of implantation of the source in the tumor.

The above mentioned U.S. Pat. No. 8,834,837 to Kelson suggests using an activity "from about 10 nanoCurie to about 10 microCurie, more preferably from about 10 nanoCurie to about 1 microCurie." U.S. patent application Ser. No. 17/343,786, which is titled: "Activity Levels for Diffusing Alpha-Emitter Radiation Therapy", suggests radon release rates which are sufficiently high to destroy a tumor and sufficiently low to avoid damage to distant healthy tissue, for various tumor types.

US patent publication 2010/0015042 to Keisari et al. mentions in-vivo experiments which used radon-224 activities in the range of 10-30 kBq, with radon desorption probabilities of 22-36%.

US patent publication 2013/0253255 to Van Niekerk, the disclosure of which is incorporated herein by reference, describes a brachytherapy seed carrying two disparate isotopes of the same substance.

US patent publication 2008/0249398 to Harder et al., the disclosure of which is incorporated herein by reference, describes a hybrid multi-radionuclide sealed source for use in brachytherapy.

It is generally desired to prevent the radionuclide from being washed away from the source by body fluids before the radionuclide has a chance to decay. PCT publication WO2018/207105, titled: "Polymer Coatings for Brachytherapy Devices", which is incorporated herein by reference in its entirety, describes coatings which are chosen to prevent the radionuclide from being washed, while not inhibiting the desorption of daughter nuclei from the source.

US patent publication 2002/0055667 to Mavity et al., the disclosure of which is incorporated herein by reference in its entirety, describes radionuclides with bio-absorbable structures that have a predefined persistence period which is usually substantially greater than the half-life of the radionuclides. The radionuclides remain localized and sequestered at a desired target site while significant radioactivity remains.

U.S. Pat. No. 8,821,364 to Fisher et al., the disclosure of which is incorporated herein by reference in its entirety, describes a brachytherapy seed made up of microspheres containing an alpha-particle-emitting radiation source and a resorbable polymer matrix, which rapidly dissolves.

SUMMARY OF THE INVENTION

Applicant has identified that there is a substantial difference in the amount of radiation which takes part in destruction of tumor cells between the interior of the tumor and areas close to the perimeter of the tumor. Close to the perimeter, the tissue of the tumor is non-necrotic and there is a rich blood supply although the vascular architecture may be disorganized and chaotic. This rich blood supply reduces the effectiveness of the alpha radiation by two effects: (1) the tumor tissue in the areas near the perimeter has a dense membrane structure, which decreases the effective diffusion range of some of the daughter radionuclides, such as $^{220}$Rn and $^{212}$Pb, and (2) $^{212}$Pb is cleared at a high rate by the blood vessels and therefore fewer alpha particles are emitted in the areas near the perimeter of the tumor. As a result, the range of destruction of tumor cells in areas near the perimeter of the tumor is low and some areas of the tumor do not receive sufficient radiation.

In addition, the extent of destruction of tissue cells depends strongly on the distance from the source. It is therefore desired to cover the tumor with a regular arrangement of sources, e.g., a hexagonal arrangement, with a low spacing, such as a spacing shorter than 5 millimeters or even not more than 4 millimeters. Still, some points of the tumor are relatively far from any of the sources when depending only on alpha radiation.

Embodiments of the present invention relate to providing radiotherapy sources, which in addition to providing alpha-radiation, through diffusing alpha-emitters radiation therapy (DaRT), provide beta radiation at significant levels.

In some embodiments, the beta radiation is achieved by DaRT radiotherapy sources having a required radon release rate, achieved by relatively high activity and a relatively low desorption probability. The use of a low desorption probability is wasteful in that a larger than necessary portion of the radionuclides on the source do not contribute to the alpha-radiation cell destruction. However, the higher activity allowed by the low desorption probability provides increased beta radiation, which can contribute to the tumor destruction. Achieving the beta destruction by the same radionuclides as provide the alpha radiation is simpler than providing separate radionuclides for the beta radiation, and this outweighs the waste in the low desorption probability.

There is therefore provided in accordance with embodiments of the present invention, an interstitial source, comprising a base suitable for implanting in a tumor; and alpha emitting atoms attached to the base, with a concentration of at least 6 µCi per centimeter length, wherein the alpha emitting atoms are attached to the base, with a desorption probability upon radioactive decay of between 2%-30%.

Optionally, the alpha emitting atoms attached to the base include at least 8 micro-Curie (µCi) per centimeter length of the base, at least 10.5 micro-Curie (µCi) per centimeter length of the base or even at least 12 micro-Curie (µCi) per centimeter length of the base. Optionally, the alpha emitting atoms comprise radium-224 atoms. Optionally, the alpha emitting atoms have a radon release rate of at least 0.5 microcurie per centimeter length. Optionally, the alpha emitting atoms have a desorption probability upon decay of at least 4%, at least 5%, at least 7%, or even at least 10%. Optionally, the alpha emitting atoms have a desorption probability upon decay of not more than 27%, less than 24% or even less than 20%.

Optionally, the alpha emitting atoms are attached to the base by a heat treatment. Optionally the alpha emitting atoms are attached to the base with a desorption probability of less than 15%. In some embodiments, the source includes a coating of a low-diffusion polymer covering the alpha emitting atoms in a manner which reduces the desorption probability of daughter radionuclides. Optionally, the coating has a thickness of at least 0.5 microns. Alternatively or additionally, the coating comprises a non-metallic coating. In some embodiments, the source includes an atomic layer deposition coating of aluminum oxide covering the alpha-emitting atoms. Optionally, the atomic layer deposition coating has a thickness of at least 2 nanometers. In some embodiments, the interstitial source additionally emits beta radiation, and wherein a ratio between an asymptotic dose of the beta radiation at a distance of 2 millimeters from the device, to a radon release rate from the device, is greater than 15 Gy/(microcurie/cm). Optionally, at least 90% of the beta radiation is emitted from progeny of the alpha emitting atoms. Optionally, at least 20% of the beta radiation is emitted from an isotope which does not emit alpha radiation.

There is further provided in accordance with embodiments of the present invention, an interstitial source, comprising a base suitable for implanting in a tumor; and alpha emitting atoms attached to the base, with a concentration of at least 10.5 µCi per centimeter length. Optionally, the alpha emitting atoms attached to the base include at least 12 micro-Curie (µCi) per centimeter length of the base. Optionally, the alpha emitting atoms attached to the base include at least 15 micro-Curie (µCi) per centimeter length of the base. Optionally, the alpha emitting atoms attached to the base include at least 21 micro-Curie (µCi) per centimeter length of the base. Optionally, the alpha emitting atoms comprise radium-224 atoms.

There is further provided in accordance with embodiments of the present invention, an interstitial source, comprising a base suitable for implanting in a tumor; and alpha emitting atoms attached to the base by heat treatment, with a desorption probability upon radioactive decay, of between 5%-30%. Optionally, the alpha emitting atoms attached to the base include at least 5 micro-Curie (µCi) per centimeter length of the base, at least 8 micro-Curie (µCi) per centimeter length of the base, at least 11 micro-Curie (µCi) per centimeter length of the base or even at least 14 micro-Curie (µCi) per centimeter length of the base.

There is further provided in accordance with embodiments of the present invention, an interstitial source, comprising a base suitable for implanting in a tumor; and alpha emitting atoms attached to the base, with a desorption probability upon radioactive decay, of between 5%-30%, wherein the interstitial source does not include a metallic coating above the alpha emitting atoms.

Optionally, the alpha emitting atoms attached to the base include at least 5 micro-Curie (µCi) per centimeter length of the base. Optionally, the alpha emitting atoms attached to the base include at least 8 micro-Curie (µCi) per centimeter length of the base. Optionally, the alpha emitting atoms attached to the base include at least 11 micro-Curie (µCi) per centimeter length of the base. Optionally, the alpha emitting atoms comprise radium-224 atoms. Optionally, the alpha emitting atoms have a desorption probability upon decay of at least 7%. Optionally, the alpha emitting atoms have a desorption probability upon decay of at least 9%. Optionally, the alpha emitting atoms are attached to the base with a desorption probability of at least 12%. Optionally, the alpha emitting atoms have a desorption probability upon decay of not more than 27%. Optionally, the alpha emitting atoms are attached to the base with a desorption probability of less than 25%. Optionally, the alpha emitting atoms are attached to the base with a desorption probability of less than 21%. Optionally, the alpha emitting atoms are attached to the base by a heat treatment. Optionally, the alpha emitting atoms are attached to the base with a desorption probability of less than 15%. In some embodiments, the source includes a coating of a low-diffusion polymer covering the alpha emitting atoms in a manner which reduces the desorption probability of daughter radionuclides. Optionally, the coating has a thickness of at least 0.5 microns. In some embodiments, the source includes an atomic layer deposition coating of aluminum oxide covering the alpha-emitting atoms. Optionally, the atomic layer deposition coating has a thickness of at least 2 nanometers.

There is further provided in accordance with embodiments of the present invention, an interstitial source, comprising a base suitable for implanting in a tumor; and radioactive atoms of one or more isotopes, which are attached to the base, wherein the radioactive atoms have a radon release rate of at least 0.5 microCurie per centimeter, and emit beta radiation achieving at 2 millimeters from the base an asymptotic dose of at least 10 Gy, wherein the ratio between the beta radiation asymptotic dose at a distance of 2 millimeters from the device, to the radon release rate, is greater than 15 Gy/(microcurie/cm).

Optionally, the ratio between the asymptotic dose at a distance of 2 millimeters from the device, to the radon release rate, is greater than 20 Gy/(microcurie/cm). Optionally, the radioactive atoms include Radium-224 atoms having an activity of at least 1 microCurie per centimeter length. Optionally, the radioactive atoms include Radium-224 atoms having an activity of at least 10.5 microCurie per centimeter length. Optionally, the radioactive atoms of one or more isotopes include one or more isotopes which do not emit alpha radiation, which emit beta radiation achieving at 2 millimeters from the base an asymptotic dose of at least 5 Gy.

DETAILED DESCRIPTION OF EMBODIMENTS

An aspect of some embodiments of the invention relates to radiotherapy sources carrying alpha emitting atoms in a manner which allows desorption of daughter radionuclides with a significant probability (e.g., at least 1%), but the desorption probability is lower than 30%. With a low desorption probability, the activity on the source can be increased without changing the radon release rate and the resulting systemic alpha radiation reaching distant healthy tissue. The increase in activity on the source increases the beta radiation provided by the source, which supplements the alpha radiation in the destruction of tumor cells.

Figure 1:
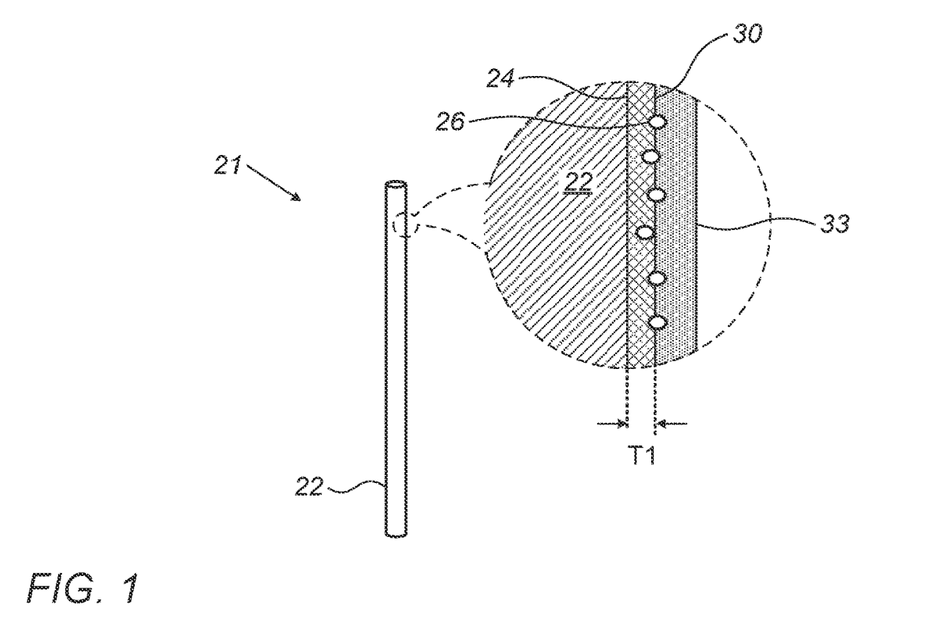
FIG. 1 is a schematic illustration of a radiotherapy source, in accordance with an embodiment of the present invention.

FIG. 1 is a schematic illustration of a radiotherapy source 21, in accordance with an embodiment of the present invention. Radiotherapy source 21 comprises a support 22, which is configured for insertion into a body of a subject, and radionuclide atoms 26 of an alpha-emitting substance, such as radium-224, an outer surface 24 of support 22. It is noted that for ease of illustration, atoms 26 as well as the other components of radiotherapy source 21, are drawn disproportionately large. In some embodiments, a coating 33 covers support 22 and atoms 26, in a manner which controls a rate of release of the radionuclide atoms 26 and/or of daughter radionuclides of atoms 26, upon radioactive decay. In some embodiments, as shown in FIG. 1, in addition to coating 33, an inner coating 30 of a thickness T1 is placed on support 22 and the radionuclide atoms 26 are attached to inner coating 30. It is noted, however, that not all embodiments include inner coating 30 and instead the radionuclide atoms 26 are attached directly to the source 21. Likewise, some embodiments do not include coating 33.

Support 22 comprises, in some embodiments, a seed for complete implant within a tumor of a patient, and may have any suitable shape, such as a rod or plate. Alternatively to being fully implanted, support 22 is only partially implanted within a patient and is part of a needle, a wire, a tip of an endoscope, a tip of a laparoscope, or any other suitable probe.

In some embodiments, support 22 is cylindrical and has a length of at least 2 millimeters, at least 5 millimeters or even at least 10 millimeters. Optionally, support 22 has a length which is smaller than 70 mm, smaller than 60 mm or even smaller than 40 mm (millimeters). Support 22 optionally has a diameter of 0.7-1 mm, although in some cases, sources of larger or smaller diameters are used. Particularly, for treatment layouts of small spacings, support 22 optionally has a diameter of less than 0.7 mm, less than 0.5 mm, less than 0.4 mm or even not more than 0.3 mm.

Typically, the radionuclide, the daughter radionuclide, and/or subsequent nuclei in the decay chain are alpha-emitting, in that an alpha particle is emitted upon the decay of any given nucleus. For example, the radionuclide may comprise an isotope of Radium (e.g., Ra-224 or Ra-223), which decays by alpha emission to produce a daughter isotope of Radon (e.g., Rn-220 or Rn-219), which decays by alpha emission to produce an isotope of Polonium (e.g., Po-216 or Po-215), which decays by alpha emission to produce an isotope of Lead (e.g., Pb-212 or Pb-211), as described, for example, in U.S. Pat. No. 8,894,969, which is incorporated herein by reference. Alternatively, the radionuclide comprises Actinium-225.

An amount of radiation supplied by radiotherapy device 21 to surrounding tissue depends on various parameters of the radiotherapy device. These include:
1) a desorption probability of daughter atoms of radionuclide atoms 26, upon decay,
2) a rate of release of radionuclide atoms 26 by diffusion, and
3) an amount of radionuclide atoms 26 on the source It is noted that while the risk of an overdose of radiation for a single small tumor is low, when treating large tumors and/or multiple tumors, the treatment may include implantation of several hundred sources. Therefore, the radiation provided by the sources is adjusted to prevent administering an overdose of radiation to the patient.

The amount of radionuclide atoms 26 in radiotherapy device 21 is generally given in terms of activity per centimeter length of support 22. The activity is measured herein in units of microcurie per centimeter length of the source. As the radiation dose reaching most of the tumor is dominated by radionuclides that leave the source, a measure of "radon release rate" is defined herein as the product of activity on the source and the desorption probability. For example, a source with 2 microcurie activity per centimeter length and a 40% desorption probability has a radon release rate of 0.8 microcurie per centimeter length.

The radon release rate of the source is typically at least 0.5, at least 1 or even at least 2 microcurie per centimeter length. Generally, the radon release rate is not more than 4 microcurie per centimeter length. In some embodiments, however, radon release rates of more than 4 microcurie per centimeter length, more than 4.5 microcurie per centimeter length, more than 5 microcurie per centimeter length, or even more than 6 microcurie per centimeter length are used, as applicant has identified that the risks of the radionuclides reaching remote healthy tissue are lower than previously assumed. Optionally, the radon release rate is selected according to the specific type of the tumor. Specific radon release rates which may be used are described, for example, in U.S. patent application Ser. No. 17/343,786, which is titled: "Activity Levels for Diffusing Alpha-Emitter Radiation Therapy", which is incorporated herein by reference.

Any suitable technique, such as any one or more of the techniques described in the aforementioned '969 patent to Kelson, may be used to couple atoms 26 to support 22. For example, a generating source that generates a flux of the radionuclide may be placed in a vacuum near support 22, such that nuclei recoiling from the generating source traverse the vacuum gap and are collected onto, or implanted in, surface 24. Alternatively, the radionuclide may be electrostatically collected onto support 22, by the application of a suitable negative voltage between the generating source and the support. In such embodiments, to facilitate the electrostatic collection of the radionuclide, support 22 may comprise an electrically-conductive metal, such as titanium. For example, support 22 may comprise an electrically-conducting metallic wire, needle, rod, or probe. Alternatively, support 22 may comprise a non-metallic needle, rod, or probe coated by an electrically-conductive metallic coating that comprises surface 24.

In the prior art, attempts were made to maximize the desorption probability in order to maximize tissue destruction and avoid waste of radionuclides that do not enter the tumor. In accordance with embodiments of the invention, the desorption probability is purposely set to lower than possible, in order to increase the ratio of beta radiation to alpha radiation provided by radiotherapy device 21.

The desorption probability is optionally lower than 30%, lower than 25%, lower than 20%, lower than 15%, lower than 13% or even lower than 10%. On the other hand, the desorption probability is preferably not too low and is optionally greater than 2%, greater than 4%, greater than 6% or even greater than 8%. In some embodiments, the desorption probability is greater than 10%, greater than 12% or even greater than 15%.

The desorption probability depends on the strength of the bond of radionuclide atoms 26 to support 22 and/or the type and thickness of coating 33.

In some embodiments, the reduced desorption probability is achieved by using an increased bond strength, while the coating is substantially the same as used for a high desorption probability, e.g., a thickness of less than 3 microns of a biocompatible PDMS (polydimethylsiloxane). The bond of the radionuclide atoms 26 to support 22 is generally achieved by heat treatment of the radiotherapy device 21, and the strength of the bond is controllable by adjusting the temperature and/or duration of the heat treatment. In some embodiments, the temperature used is at least 50° C., at least 100° C. or even at least 200° C., above the temperature used to achieve a desorption probability of about 38-45%. Alternatively or additionally, the heat treatment is performed at a lower pressure of below 101 millibar, below 10-2 millibar, or even less than $10^{-3}$ millibar, and/or the heat treatment is performed for a longer duration, for example at least 10 minutes, at least 20 minutes, at least 40 minutes or even at least an hour beyond the duration required to achieve a desorption probability of about 38-45%. Alternatively or additionally to reducing the desorption probability by altering the heat treatment, any other suitable method may be used to reduce the bond strength.

In some embodiments, the fixation of the radionuclides to the seed surface is performed in a noble gas environment or a vacuum environment. The fixation may be performed in any suitable pressure. The heat treatment is optionally applied for at least 10 minutes, at least 30 minutes, at least an hour, at least 3 hours or even at least 10 hours. The temperature of the heat treatment optionally depends on the pressure, the environment in which the radionuclides are fixated to the surface and the duration of the fixation process. In some embodiments, the temperature depends on the material of the seed surface.

In other embodiments, the bond strength is substantially the same as used for a desorption rate of about 38-45% and the reduced desorption probability is achieved by altering coating 33 in order to reduce the desorption probability to the desired level.

For example, in some embodiments, coating 33 comprises a layer of a polymer, which is highly permeable to the daughter radionuclide (e.g., Radon), such as a biocompatible PDMS (polydimethylsiloxane), so that the daughter radionuclide may diffuse through coating 33. For example, the diffusion coefficient of the daughter radionuclide in the polymer of coating 33 may be at least $10^{-11}$ cm$^2$/sec. In these embodiments, the thickness TO of coating 33 is optionally greater than 20 microns, greater than 50 microns, greater than 100 microns, greater than 200 microns, or even greater than 300 microns.

Alternatively or additionally to PDMS (polydimethylsiloxane), coating 33 comprises any other suitable material which is permeable to the daughter radionuclide, such as polypropylene, polycarbonate, polyethylene terephthalate, poly(methyl methacrylate), and/or polysulfone, that coats surface 24 and thus covers atoms 26.

In other embodiments, coating 33 comprises one or more layers of materials which are considerably less permeable to radon than PDMS. In some of these embodiments, coating 33 is a low-diffusion polymer (e.g., parylene-n) having a thickness of at least 0.2 microns, at least 0.5 microns, at least 1 micron or even at least 2 microns. It is noted, however, that the coating is not too thick, in order to still allow the desired rate of desorption of Radon, such that the coating optionally has a thickness of less than 100 microns, less than 20 microns, less than 5 microns, or even less than 3 microns. In some embodiments, the coating has a thickness of less than 2 microns, less than 1 micron or even less than 0.75 microns. Low-diffusion polymers are polymers in which Radon diffuses to a depth of less than 5 microns. In some embodiments, polymers with even lower diffusion depths are used, for example, less than 2 microns, less than 1 micron or even less than 0.5 microns.

Other embodiments of low permeability coatings include an atomic layer deposition (e.g., by $Al_2O_3$). The atomic layer deposition optionally has a thickness of at least 2 nanometers, at least 3 nanometers or even at least 5 nanometers. Optionally, the atomic layer deposition has a thickness of less than 15 nanometers or even less than 10 nanometers.

Optionally, in the above embodiments, coating 33 comprises a non-metallic coating which does not include metals. This is because applicant found metal coatings to be hard to work with and of low predictability of results. In other embodiments, however, coating 33 is partially or entirely a metal coating, such as titanium. Applicant found that a metal coating of suitable thickness can achieve low desorption probabilities of the daughter radon radionuclides.

The desired desorption rate is achieved, in still other embodiments, by a combination of a stronger bond (for example due to the heat treatment) and the properties of coating 33. For example, coating 33 may have a thickness greater than used for a desorption rate of about 38-45%, such as greater than 4 microns, greater than 6 microns, greater than 10 microns, greater than 20 microns, or even greater than 40 microns, but still less than 100 microns or even less than 60 microns. The additional decrease in the desorption rate is optionally achieved by changing one or more properties of the heat treatment.

The rate of release of radionuclide atoms 26, e.g., by diffusion, is, in some embodiments, very low and even negligible. In other embodiments, a substantial rate of diffusion of radionuclide atoms 26 is used, for example using any of the methods described in PCT publication WO 2019/193464, titled: "Controlled Release of Radionuclides", which is incorporated herein by reference. The diffusion is optionally achieved by using for coating 33, a bio-absorbable coating which initially prevents premature escape of radionuclide atoms 26 but after implantation in a tumor disintegrates and allows the diffusion. The rate of release of radionuclide atoms 26 is optionally lower than the rate of release of daughter radionuclides due to desorption, and is preferably less than 50%, less than 30% or even less than 10% of the rate of release of daughter radionuclides due to desorption.

Typically, the density of atoms 26 on outer surface 24 is between $10^{11}$ and $10^{14}$ atoms per square centimeter. The activity of the source is optionally selected according to the desorption rate so that the desired radon release rate is achieved. In some embodiments, the seed has a concentration of radionuclides of at least 5 µCi per centimeter length, at least 7 µCi per centimeter length, at least 8 µCi per centimeter length, or even at least 10 µCi per centimeter length, at least 11 µCi per centimeter length, at least 12 µCi per centimeter length or even at least 14 µCi per centimeter length. Optionally, the concentration of radionuclides is not higher than 15 µCi per centimeter length and in some embodiments is less than 13 µCi per centimeter length. In other embodiments, however, the concentration of radionuclides is above 15 µCi per centimeter length.

The beta radiation due to radiation device 21 carrying radium-224 results from decay of lead-212 into bismuth-212 and decay of bismuth-212 into polonium-212, or decay of bismuth-212 into thallium-208, which emits an electron when it decays to lead-208. Some of the beta radiation comes from daughter radionuclides still attached to the source, while another part of the beta radiation comes from daughter radionuclides in the tumor, after they or one of their ancestor radionuclides escaped device 21. It is noted, however, that some of the lead-212 that reaches or is created in the tumor is cleared from the tumor through the blood stream before it has a chance to decay.

Use of a relatively low desorption probability in accordance with embodiments of the present invention allows for increasing the beta radiation reaching the tumor cells in two ways. First, the low desorption probability allows for increasing the activity of radium on device 21, in a manner which increases the beta radiation but does not increase the side effects of alpha radiation of lead-212 that leaves the tumor through the blood stream. Second, the low desorption probability reduces the amount of lead-212 that leaves the tumor through the blood stream and therefore does not provide beta radiation. While Beta radiation has a larger range than alpha radiation, it still decreases quite sharply with distance from he source.

As described in Lior Arazi, "Diffusing Alpha-Emitters Radiation Therapy: Theoretical and Experimental Dosimetry", Thesis submitted to the senate of Tel Aviv University, September 2008, the disclosure of which is incorporated herein by reference, for a radiation device 21 having a radium activity of 3 microcurie per centimeter, the beta radiation contributes an asymptotic dose of about 10 Gy at a distance of 2 millimeters from the source. Increasing the radium activity of device 21 to 9 microcurie per centimeter length would bring the beta contribution to about 30 Gy at a distance of 2 millimeters from the device 21. For a hexagonal arrangement with a spacing of 4 millimeters, each point in the tumor would receive beta radiation from three sources, and thus would receive at least about 90 Gy. Beta radiation is less destructive than alpha radiation, by a factor considered to be between about 5-10, such that this 90 Gy is equivalent to about 9-18 Gy from alpha radiation.

Therefore, beta radiation can provide emissions of a therapeutic level without increasing the radon release rate beyond its desired level. In some embodiments, the radiation device 21 is designed to provide at a distance of 2 millimeters from the device, in a tumor with negligible lead clearance through the blood stream, at least 18 Gy, at least 20 Gy, at least 24 Gy, at least 28 Gy or even at least 30 Gy.

The alpha radiation provided by the radiation device 21 providing these beta radiation levels is optionally at least 10 Gy or even at least 20 Gy at a distance of 2 millimeters from the device. In some embodiments, the alpha radiation provided by the radiation device 21 is less than 100 Gy, less than 60 Gy or even less than 40 Gy. This alpha radiation is optionally provided by a radiation device 21 having a radon release rate of at least 0.5 microcurie per centimeter length, but lower than 4 microcurie per centimeter length, lower than 3 microcurie per centimeter length, lower than 2.5 microcurie per centimeter length or even lower than 2 microcurie per centimeter length. In some embodiments, the ratio between the asymptotic dose at a distance of 2 millimeters from the device, in a tumor with negligible lead clearance through the blood stream to the radon release rate of the device is greater than 15 Gy/(microcurie/cm), greater than 20 Gy/(microcurie/cm), greater than 25 Gy/(microcurie/cm), or even greater than 30 Gy/(microcurie/cm).

In the above description, the beta radiation is provided by progeny of the alpha emitting radionuclides that provide the alpha radiation. Generally, at least 90%, at least 95% or even at least 99% of the beta radiation is due to the alpha emitting radionuclides.

Alternatively or additionally to using beta radiation from the radionuclides which provide the alpha radiation to supplement the alpha radiation, the radiation doses discussed above are achieved by a device in which beta radiation is supplied by separate radionuclides which do not supply therapeutically effective alpha radiation.

Figure 2:
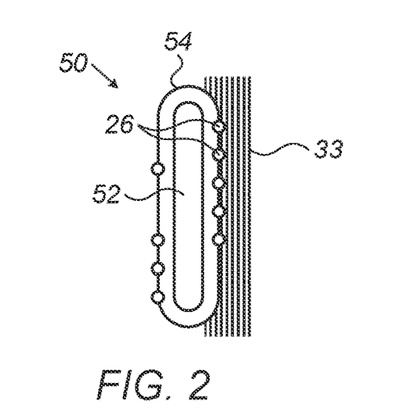
FIG. 2 is a schematic illustration of a combined alpha-radiation and beta-radiation source, in accordance with an embodiment of the invention.

FIG. 2 is a schematic illustration of a combined alpha-radiation and beta-radiation source 50, in accordance with an embodiment of the invention. Source 50 comprises a capsule 54 which encapsulates a radioactive material 52 of one or more radioisotopes, which emit beta and/or gamma radiation. Alpha-emitting radionuclide atoms 26 are attached to an outer surface of capsule 54, in a manner which allows their daughter radionuclides to leave the source 50 with a desired desorption probability, upon radioactive decay. In some embodiments, radionuclide atoms 26 are covered by a coating 33, as discussed above regarding FIG. 1. As shown, source 50 does not include a coating 30 between the surface of capsule 54 and radionuclide atoms 26. In some embodiments, however, a coating 30 is included between capsule 54 and radionuclide atoms 26.

Capsule 54 optionally comprises a sealed container which does not prevent exit of beta and/or gamma radiation therefrom. Capsule 54 optionally comprises a metal, such as gold, stainless steel, titanium and/or platinum. Alternatively, capsule 54 comprises a plastic, such as described in U.S. Pat. No. 7,922,646, titled "Plastic Brachytherapy sources", which is incorporated herein by reference. Optionally, in accordance with this alternative, the plastic capsule is coated by a thin metal coating to which radionuclide atoms 26 are attached. Capsule 54 is of any suitable size and/or shape known in the art, such as described, for example in U.S. Pat. No. 6,099,458, titled: "Encapsulated Low-Energy Brachytherapy Sources" and/or U.S. Pat. No. 10,166,403, titled: "Brachytherapy Source Assembly", the disclosures of which are incorporated herein by reference.

Radioactive material 52 comprises one or more radioactive isotopes which emit beta radiation, such as iridium-192, californium-252, gold-198, indium-114, phosphorus-32, radium-226, ruthenium-106, samarium-145, strontium-90, yttrium-90, tantalum-182, thulium-107, tungsten-181 and/or ytterbium-169. Alternatively, radioactive material 52 comprises one or more radioactive isotopes which emit gamma radiation, such as iodine 125 (I-125), palladium 103 (Pd-103), cesium 131 (Cs-131), cesium 137 (Cs-137) and/or cobalt 60 (Co-60). Other suitable radioactive materials known in the art may also be used, as well as combinations of a plurality of beta emitters, combinations of a plurality of gamma emitters, combinations of a beta emitters and gamma emitters and/or one or more substances which emit both beta and gamma radiation.

The activity of radioactive material 52 and the thickness of the walls of capsule 54 are selected to achieve a sufficient amount of radiation at a distance of about 3-4 mm from source 50. Optionally, radioactive material 52 has an activity level of at least 0.5 mCi (millicurie), at least 5 mCi, at least 20 mCi, or even at least 50 mCi. In some embodiments, the activity of radioactive material 52 is substantially higher, above 100 mCi, above 200 mCi or even above 500 mCi.

In some embodiments, radioactive material 52 fills capsule 54. Alternatively, radioactive material 52 is placed as an inner coating on the walls of capsule 54.

Figure 3:
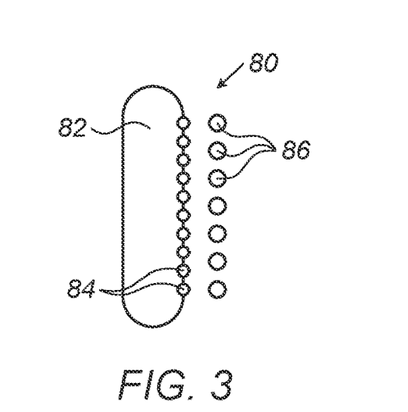
FIG. 3 is a schematic illustration of a combined alpha-radiation and beta-radiation source, in accordance with another embodiment of the invention.

FIG. 3 is a schematic illustration of a combined alpha-radiation and beta-radiation source 80, in accordance with another embodiment of the invention. Source 80 comprises a base 82 which has beta-emitting radionuclides 84 attached thereto, directly or through one or more coatings. Alpha-emitting radionuclides 86 are placed above beta-emitting radionuclides 84, either directly attached to the beta-emitting radionuclides 84 or placed on a coating which separates beta-emitting radionuclides 84 from alpha-emitting radionuclides 86.

Figure 4:
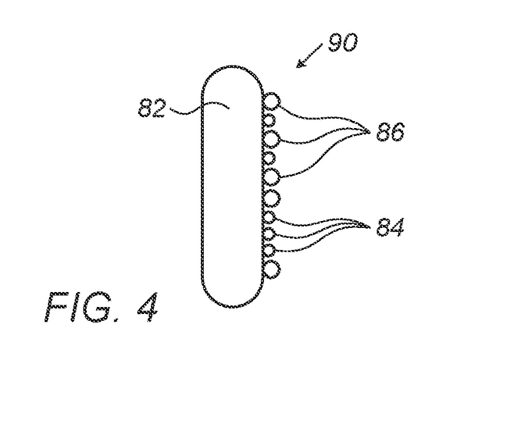
FIG. 4 is a schematic illustration of a combined alpha-radiation and beta-radiation source, in accordance with still another embodiment of the invention.

FIG. 4 is a schematic illustration of a combined alpha-radiation and beta-radiation source 90, in accordance with still another embodiment of the invention. In source 90, beta-emitting radionuclides 84 and alpha-emitting radionuclides 86 are spread out on the surface of base 82.

In sources 80 and 90, the beta-emitting radionuclides 84 are mounted on base 82 in a manner which substantially prevents their escape from source 80. In contrast, alpha-emitting radionuclides 86 are mounted on base 82 in a manner which allows escape of daughter radionuclides from source 80 upon decay.

In sources 50, 80 and 90, the daughter radionuclides optionally escape source 80 with a desorption probability of at least 30%, at least 35% or even at least 40% and the activity of alpha-emitting radionuclides 86 is set accordingly to levels known in the art for such desorption probability levels, lower than those discussed above regarding radiotherapy device 21. This is because, in the embodiments of sources 50, 80 and 90, the beta radiation is optionally supplied mainly by beta-emitting radionuclides 84 and the alpha-emitting radionuclides 86 are not trusted for beta radiation.

Alternatively, a desired level of beta radiation, for example at least 60 gray (Gy), at least 70 Gy or even at least 80 Gy, is supplied by a combination of beta radiation from beta-emitting radionuclides 84 and alpha-emitting radionuclides 86. In some embodiments, at least 10%, at least 20%, at least 30% or even at least 40% of the beta radiation emitted by sources 50, 80 and 90 is emitted from alpha-emitting radionuclides 86. Alternatively or additionally, at least 10%, at least 20%, at least 30% or even at least 40% of the beta radiation emitted by sources 50, 80 and 90 is emitted from beta-emitting radionuclides 84.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include,"

"have" and their conjugates, shall mean, when used in the claims, "including but not necessarily limited to."

The invention claimed is:

1. An interstitial source, comprising:
a base suitable for implanting in a tumor;
alpha emitting atoms attached to the base, with a concentration of at least 6 µCi per centimeter length; and
a coating of a low-diffusion polymer covering the alpha emitting atoms in a manner which reduces the desorption probability of daughter radionuclides,
wherein the alpha emitting atoms are attached to the base, with a desorption probability upon radioactive decay of not more than 30%.

2. The source of claim 1, wherein the alpha emitting atoms attached to the base include at least 8 micro-Curie (µCi) per centimeter length of the base.

3. The source of claim 2, wherein the alpha emitting atoms attached to the base include at least 10.5 micro-Curie (µCi) per centimeter length of the base.

4. The source of claim 3, wherein the alpha emitting atoms attached to the base include at least 12 micro-Curie (µCi) per centimeter length of the base.

5. The source of claim 1, wherein the alpha emitting atoms comprise radium-224 atoms.

6. The source of claim 1, wherein the alpha emitting atoms have a desorption probability upon decay of at least 2%.

7. The source of claim 6, wherein the alpha emitting atoms have a desorption probability upon decay of at least 5%.

8. The source of claim 1, wherein the alpha emitting atoms have a radon release rate of at least 0.5 microcurie per centimeter length.

9. The source of claim 1, wherein the alpha emitting atoms have a desorption probability upon decay of not more than 27%.

10. The source of claim 9, wherein the alpha emitting atoms are attached to the base with a desorption probability of less than 24%.

11. The source of claim 10, wherein the alpha emitting atoms are attached to the base with a desorption probability of less than 20%.

12. The source of claim 11, wherein the alpha emitting atoms are attached to the base by a heat treatment.

13. The source of claim 12, wherein the alpha emitting atoms are attached to the base with a desorption probability of less than 15%.

14. The source of claim 1, wherein the coating has a thickness of at least 0.5 microns.

15. The source of claim 1, wherein the coating comprises a non-metallic coating.

16. An interstitial source, comprising:
a base suitable for implanting in a tumor;
alpha emitting atoms attached to the base, with a concentration of at least 6 µCi per centimeter length; and
an atomic layer deposition coating of aluminum oxide covering the alpha-emitting atoms,
wherein the alpha emitting atoms are attached to the base, with a desorption probability upon radioactive decay of not more than 30%.

17. The source of claim 16, wherein the atomic layer deposition coating has a thickness of at least 2 nanometers.

18. The source of claim 16, wherein the alpha emitting atoms attached to the base include at least 8 micro-Curie (µCi) per centimeter length of the base.

19. The source of claim 18, wherein the alpha emitting atoms attached to the base include at least 10.5 micro-Curie (µCi) per centimeter length of the base.

20. The source of claim 19, wherein the alpha emitting atoms attached to the base include at least 12 micro-Curie (µCi) per centimeter length of the base.

21. The source of claim 16, wherein the alpha emitting atoms comprise radium-224 atoms.

22. The source of claim 16, wherein the alpha emitting atoms have a desorption probability upon decay of at least 2%.

23. The source of claim 22, wherein the alpha emitting atoms have a desorption probability upon decay of at least 5%.

24. The source of claim 16, wherein the alpha emitting atoms have a radon release rate of at least 0.5 microcurie per centimeter length.

25. The source of claim 16, wherein the alpha emitting atoms are attached to the base with a desorption probability of less than 24%.

26. The source of claim 25, wherein the alpha emitting atoms are attached to the base with a desorption probability of less than 20%.

27. The source of claim 26, wherein the alpha emitting atoms are attached to the base by a heat treatment.

28. The source of claim 27, wherein the alpha emitting atoms are attached to the base with a desorption probability of less than 15%.

29. An interstitial source, comprising:
a base suitable for implanting in a tumor; and
alpha emitting atoms attached to the base, with a concentration of at least 6 Ci per centimeter length,
wherein the alpha emitting atoms are attached to the base, with a desorption probability upon radioactive decay of not more than 30%, and
wherein the interstitial source additionally emits beta radiation, and wherein a ratio between an asymptotic dose of the beta radiation at a distance of 2 millimeters from the interstitial source, to a radon release rate from the interstitial source, is greater than 15 Gy/(microcurie/cm).

30. The source of claim 29, and comprising a coating of a low-diffusion polymer covering the alpha emitting atoms in a manner which reduces the desorption probability of daughter radionuclides.

31. The source of claim 29, wherein at least 90% of the beta radiation is emitted from progeny of the alpha emitting atoms.

32. The source of claim 29, wherein at least 20% of the beta radiation is emitted from an isotope which does not emit alpha radiation.

* * * * *